United States Patent [19]

Adamski et al.

[11] Patent Number: 5,403,963
[45] Date of Patent: Apr. 4, 1995

[54] PROCESS FOR THE PRODUCTION OF LOWER ALCOHOLS

[75] Inventors: Robert P. Adamski, Missouri City; George C. Blytas, Houston, both of Tex.

[73] Assignee: Shell Oil Company, Houston, Tex.

[21] Appl. No.: 189,621

[22] Filed: Feb. 1, 1994

[51] Int. Cl.⁶ .................. C07C 29/06; C07C 31/10; C07C 31/12
[52] U.S. Cl. .......................... 568/888; 558/43
[58] Field of Search ........................... 568/888

[56] References Cited

U.S. PATENT DOCUMENTS

| | | | |
|---|---|---|---|
| 2,055,763 | 9/1936 | Greer et al. | 568/888 |
| 2,467,846 | 4/1949 | Mottern et al. | 568/888 |
| 2,629,747 | 2/1953 | Fugua | 568/888 |
| 3,277,190 | 10/1966 | Cofer et al. | 568/888 |
| 4,538,010 | 8/1985 | Diana, I et al. | 568/888 |
| 4,760,201 | 7/1988 | Diana, II et al. | 568/888 |
| 4,761,505 | 8/1988 | Diana, III et al. | 568/888 |

FOREIGN PATENT DOCUMENTS 637414 5/1950 United Kingdom ............... 568/888

Primary Examiner—Joseph E. Evans
Attorney, Agent, or Firm—Todd F. Volyn

[57] ABSTRACT

A process for producing lower alcohols is presented in which an olefinic feed and $H_2SO_4$ react to form a mixture comprising alkyl sulfates, alkyl disulfates, fat acid, and nonpolar hydrocarbons. The mixture is separated into two phases, a nonpolar phase comprising nonpolar hydrocarbons and a polar phase comprising alkyl sulfates, alkyl disulfates, and fat acids. A rag-layer that forms between the nonpolar and polar phases comprising carbonaceous particulate material is removed by contact with an extraction reagent. This can be a slip stream comprising an etheric derivative of the olefinic feed and an oligomeric derivative of the feed which is withdrawn from a subsequent step the process. This forms a separate hydrocarbon phase which is then extracted. The sulfates are then hydrolyzed to form alcohol.

15 Claims, 2 Drawing Sheets

PROCESS FOR THE PRODUCTION OF LOWER ALCOHOLS

BACKGROUND OF THE INVENTION

This invention relates to the production of lower alcohols. The production of lower alcohols such as butyl or propyl alcohols are among the most commercially significant operations undertaken in the chemical industry. The principle means by which these alcohols are manufactured is through the hydration of olefins. Hydration may either be direct, wherein an olefin is catalytically reacted with water, or it may be indirect. In indirect hydration processes olefinic starting materials are passed into a mixture of sulfuric acid and water. Intermediate carbonium ions are formed at the site of the double bond in the starting material. These carbonium ions then react with sulfate ions to form alkyl hydrogen sulfate and dialkyl sulfates which are then reacted with water to give the alcohols.

In industrial applications, many factors complicate these otherwise straightforward indirect hydration reactions. For example, numerous intermediate and products of side reactions such as etheric derivatives of the reactants accompany the production of the desirable alcohol products. Where production accompanies petroleum based refinery operations, it is not uncommon to have feeds mixed with small amounts of other substances. For example, in the production of secondary butanol from butylene it is not uncommon to have small amounts of isobutylene, isopentene, and other impurities mixed with the desired n-butylene feeds. This can result in copolymerization of these species along with the production of the desired products. Octylene, hexadecene, dodecene, and high homologues have been identified as several oligomeric and polymeric substances that readily form in this process. These polymeric substances result from exhaustive dehydration, affected by concentrated $H_2SO_4$, of the various oligomeric species of alcohols and ethers, with very small contribution from sulfonated and sulfated species. Elemental analysis yields a typical composition of $C_8H_{12}O_1S_{0.1}$. These substances and others contribute to the presence of undesirable carbonaceous particulate matter. Other impurities are also generated in these processes such as ethers, diethers, sulfated versions of polymeric, oligomeric, and other byproducts. Even beyond creating a yield loss of desired product, these polymeric impurities create significant problems in processing operations. In one method of creating high purity product, phase separators follow reaction vessels so that fat acid intermediates and undesirable or unreacted hydrocarbons can be separated. Thereafter, the hydrocarbons are either recycled or used in other processes. The presence of polymers can show up in separators as a rag layer between the two phases. Tight emulsions can form so that separation becomes more complex and takes more time thereby diminishing the efficiency of the process.

Additional problems include excess hydrocarbon entrainment and acid carryover in steps required to separate or finish the desired product. In the production of secondary butanol, for example, butylene is frequently entrained to fat acids after olefin hydration. Separation of the desired product typically requires at least one stripping step. The presence of polymeric impurities can cause phase separation problems resulting in excess butylene entrainment. This causes foaming in the strippers which also reduces process efficiency.

Further still, the presence of solids in steps involving liquid flow can cause innumerable mechanical problems such as fouling transmission lines, clogging valves, and clogging filters. In spite of the problems created by the presence of polymers in alcohol production, some of the polymers have utility. For example, some $C_4$ and $C_5$ based oligomers can be added to good effect in gasoline blends. Thus, removing such impurities from alcohol production processes could not only allow the production of alcohols to proceed more efficiently but could also provide a mechanism for capturing useful byproduct for subsequent use elsewhere such as in gasoline blending.

Removal of polymeric and carbonaceous materials from butyl alcohol production would greatly enhance the efficiency and economics of production. Unfortunately, many conventional methods have proven unacceptable to accomplish these objectives. A liquid phase water/caustic/water wash sequence of phase separated crude secondary butyl alcohol, for example, is known in the art. It is useful for the removal of some unwanted substances such as unreacted $C_4$ entrained to acid. However, this process does little to remove solid polymeric species.

One approach taken to address these problems is to discard or continuously draw off $H_2SO_4$ so that entrained materials are removed with it. U.S. Pat. Nos. 3,227,774, 3,462,512 and 3,691,252 to Goldsby disclose methods employing this technique. In these methods, polymeric oils are removed by an acid extraction in isobutane. Unfortunately, this method does not apply to the removal of particulate matter and requires careful control of reaction conditions to avoid yet further polymerization. Further, a considerable amount of acid is "spent" and must be disposed. Continuously feeding $H_2SO_4$ to compensate for that which is drawn off can become rather expensive.

U.S. Pat. No. 3,733,368 to Dodd et al. discloses a method for removing polymeric impurities in the catalytic hydration of ethylene to ethanol. This involves exposing an ethylene recycle stream to a series of two separate treatments with different scrubbing reagents. Only lighter polymeric impurities are effected. U.S. Pat. No. 4,762,616 to Litzen et al. provides a method for removing polymeric impurities from isopropyl alcohol. This occurs only during the finishing phase of alcohol production. It is a purification method after the bulk of the process reactions have already occurred. Both of these patents are broadly representative of prior art methods for impurity removal; the focus is on cleaning the products or their precursors rather than on purifying the acid during the hydration process.

Rindtorff et al., Canadian Pat. 703,171, prevent introduction of polymeric material into recycle streams of ethylene in a similar process. In this process, the entire hydration reactor product is washed first with ethanol and then with water. The use of other solvents such as benzene and toluene is also disclosed. Still, the product of this wash step joins the aqueous ethanol stream to be purified downstream. Thus, the impurities therein dissolved can form incrustations resulting in problems in subsequent steps similar to those noted above.

Throughout much of the prior art, removal of impurities from alcohol production is facilitated by maintaining the substances to be treated in the gaseous state. The Rindtorff process above and U.S. Pat. Nos. 3,953,533 and 4,351,970 to Sommer et al, share this characteristic. Each is designed for the olefinic hydration at high temperatures and is inapplicable to the removal of polymers in process steps that might otherwise be conducted in the liquid state.

Processes for producing lower alcohols by the hydration of olefins could be made much more efficient and economically beneficial if polymeric impurities could be removed during the course of the reactions. This is particularly true where such processes occur in the liquid state. Safety concerns and other factors which make operating with vaporized reactants unattractive, increasingly make such liquid state operations desirable. Eliminating fouling agents from entering the mechanical components of these processes and reducing detracting phase changes such as foaming is greatly needed.

SUMMARY OF THE INVENTION

It is an object of this invention to provide an improved method for producing lower alcohols.

It is a further object of this invention to provide a method for removing impurities from the production of lower alcohols by the indirect hydration of olefins.

It is a further object of this invention to provide a method for making the production of lower alcohols by the indirect hydration of olefins more efficient by enabling $H_2SO_4$ to be recirculated without substantial loss. Recycling water used in the process is also within the kin of this object of the invention.

It is a yet further object of this invention to provide a method for the removal of carbonaceous and polymeric substances that appear in the production of butyl alcohols by the hydration of olefins; particularly solid particulate substances.

In accordance with this invention a process is provided for producing lower alcohols comprising:
reacting an olefinic feed with $H_2SO_4$;
treating the $H_2SO_4$ with an extraction reagent so that carbonaceous particulate matter formed during the reaction is substantially removed from the $H_2SO_4$; and
recirculating the $H_2SO_4$ to the reaction without substantial diminution.

In a further embodiment of the invention, the olefinic feed and the $H_2SO_4$ are reacted in a first reactor to form a first mixture comprising alkyl sulfates, dialkyl sulfates, fat acid, and nonpolar hydrocarbons;
the first mixture is separated into two phases, a nonpolar phase comprising nonpolar hydrocarbons and a polar phase comprising alkyl sulfates, dialkyl sulfates and fat acids, the nonpolar and polar phases have a rag-layer comprising carbonaceous material between them;
the rag-layer is contacted with an extraction reagent so that the carbonaceous material may be removed from the process, the extraction reagent comprises ether derivatives of the olefinic feed and oligomeric derivatives of the olefinic feed; and
the alkyl sulfates and the dialkyl sulfates are subjected to hydrolysis to form the lower alcohol.

An even greater degree of carbonaceous product removal is attained by adding water to the rag layer before or after adding the extraction reagent. This water can be a slip stream from the hydration step or can be additional water added to the process. As used throughout this specification, a slip stream is a portion withdrawn from a stream in a processor step. One skilled in the art will readily appreciate that slip streams are frequently used to conduct quality control measurements and undertake process control measures among other functions.

Alternatively, the processes of the instant invention may incorporate the use of solvents such as toluene and other aromatics as an extraction reagent or may use a combination of nonparaffinic/nonolefinic extraction reagents in concert with downstream products of the olefinic feed. The methods of this invention can be used in conjunction with existing industrial methods for producing secondary alcohols and thereby increase their efficiency, reduce their tendency to fouling and other problems, and increase product yields.

As a consequence of the practice of this invention high quality lower alcohols are produced with a greater economic return than has been possible in the past.

DETAILED DESCRIPTION OF THE INVENTION

Figure 1:
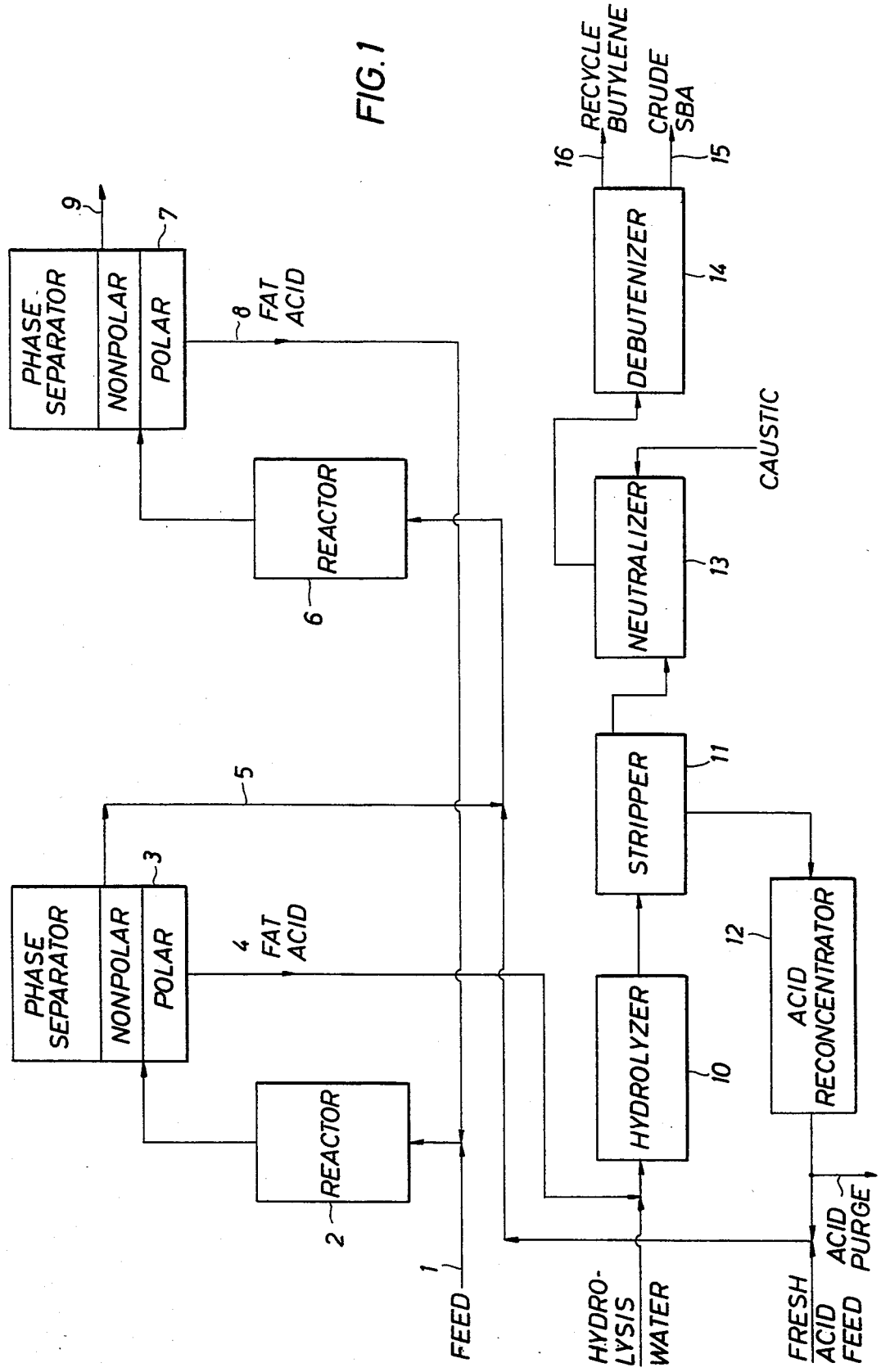
FIG. 1 is a flow diagram of a butyl alcohol production process. A carbonaceous particle removal step is not included.

A new method has been found for the removal of carbonaceous materials in the preparation of lower alcohols from the indirect hydration of olefins. In this new method, olefinic feed is reacted with sulfuric acid to produce alkyl sulfates and dialkyl sulfates. Typically, these reactions will be accompanied by the production of alkyl ethers, oligomers, polymers, and copolymers. This new method provides a tremendous improvement in the efficiency and economics of lower alcohol production by reducing or eliminating the need to purge acid, substantially reducing fouling of mechanical devices, and rendering uncontaminated chemical intermediates and products.

The process herein claimed is an indirect hydration of olefinic feeds. In industrial applications, typically a phase separator is used to separate the products of the initial reaction from unreacted feed. Separation is usually based upon product polarity so that two layers, a polar layer and nonpolar layer, are formed. Unreacted feed and other hydrocarbons that have not proceeded to hydration are present in the nonpolar layer. Fat acids, alkyl sulfates, and dialkyl sulfates are in the polar layer. At this point, the presence of particulate or carbonaceous impurities is noticeable. Generally, the impurities will form as a rag layer between the polar and nonpolar layers.

Removing particulate matter present in the rag layer can be conducted by solvent extraction. In one approach, solvents such as toluene o-xylene 1-methyl-naphthalene, and other aromatic compounds may be added to the rag layer for the extraction of particulate matter. Other solvents can also be used such as etheric and oligomeric derivatives of the feed, however, olefinic and paraffinic substances are generally not useful as solvents. Mixtures of solvents are also useful in this regard. However, toluene is a preferred extraction solvent, particularly when the process is the production of secondary butanol.

In a more preferred approach, a slip stream from a downstream step in the alcohol production process is introduced into the rag layer and is used as the extraction reagent. Downstream step is used herein to denote a step subsequent to the initial reaction of olefinic feed with $H_2SO_4$ in the process for producing lower alcohols by indirect hydration. The slipstream will generally contain a mixture of the alkyl ether derivatives of the olefinic feed formed as part of the hydration of the olefin and some lower weight oligomers that are also derivatives of the olefinic feed. Preferably, a slipstream is selected which comprises etheric derivatives of the olefinic feed, oligomeric derivatives of the olefinic feed, polymeric derivatives of the olefinic feed, or mixtures of all or some of these substances.

Without being bound to theory, it has been found that whether the removal of carbonaceous material is conducted with the use of a solvent extraction step or a slipstream comprising downstream intermediates, extraction is best affected by substances which are not entirely nonpolar. Thus, the use of most paraffinic or olefinic materials is not favored. Further, substances that are too polar are not generally favored for use in the extraction of carbonaceous material since these may be too miscible with the polar acid phase.

Again without being bound to theory, it is believed that the solids must be wetted by the solvent or extraction reagent so that they can be floated out of the denser acid. Then they are subject to removal and leave behind a purified acid. The further addition of water can enhance this step by further enabling the flotation of particulate matter to the top of the acid. The addition of water decreases hydrocarbon miscibility in the acid. Hydrocarbons released from the fat acid wet the solids, thereby lowering the density of the solids. Thus, the range of materials that can be selected for use in this process is fairly broad; they should be selected from among substances which are not entirely nonpolar and wet the impurities sought to be removed.

In a most preferred embodiment, sec-butanol is produced by the hydration of butylene in sulfuric acid. Butyl hydrogen sulfate and dibutyl sulfate are formed as intermediates along with the production of polymeric and carbonaceous impurities as well as other impurities. A stream comprising sec-butyl ether and $C_4$ oligomers is taken as the tops product of a downstream step. This stream of tops products is used as an extraction reagent for the removal of polymeric and other carbonaceous materials.

Once the appropriate extraction reagent is withdrawn from the downstream process, it is contacted with the fat acid and rag layer found in the phase separator following reaction of olefinic feed with sulfuric acid. Preferably, this is done in a static mixer. The extraction reagent will extract polymeric and other carbonaceous products from this slip stream. Thereafter, the polymer and other carbonaceous products are removed. This extraction step can also be performed on subsequent reactions between olefin and sulfuric acid as where a recycle current or multistep reaction is employed.

The addition of water to the rag layer before or after the contents of the rag layer are contacted by either a solvent or a stream of extraction reagent from a downstream process is even more preferred. All or part of the water may be taken from the subsequent hydration step of the process. There is no known limit to the amount of water that can be added but it has been found that between about 0.2 and 2 volumes of water per volume of $H_2SO_4$ would be adequate. Equal volumes of water and acid have been found to work particularly well. The use of water from the hydration step is particularly preferred since this maximizes process efficiency and economics.

It is most surprising that the introduction of a substance containing polymers or oligomers derived from olefinic feed can be used to extract impurities. Rather, one would have expected an additive effect. That is, one would have expected to see an increase in the total polymer content of the rag layer. Nevertheless, this method has been found most effective.

Referring now to the drawings, FIG. 1 is a flow diagram of a commercial process for preparing butyl alcohols by hydrating olefins. A butylene feed is introduced at 1. The feed may originate from stored $C_4$ materials, it may be the product of other refinery processes, or it may be the recycle stream of $C_4$ drawn from elsewhere in this process. In one embodiment, the feed comprises 75.8% w n-butylene, 0.2% w isobutylene, 0.1% w amylenes, 10 ppm sulphur, and 23.9% w butane with a feed rate in excess of 8,000 lbs/hour. All weight percents are based on the total weight of feed. Low iso-butylene and amylene contents contribute to the minimization of polymer formation and a low sulphur level reduces odorific qualities of the finished product. Otherwise, it must be noted that the precise composition of feed makes little difference to this invention provided that olefinic starting material is present. The same general process is used in the production of other lower alcohols with feeds differing depending upon the alcohol product desired. Thus, for example, one could select a feed comprising propylene to produce propanol.

The feed is reacted with $H_2SO_4$ in a first reactor 2. In the embodiment in which over 8000 lbs/hour of feed are introduced, over 13,000 lbs/hour of $H_2SO_4$ are fed into reactor 2. Generally, this sulfuric acid is maintained at greater than 70% w by total weight of acid. Of course, quantities and strength of $H_2SO_4$ will vary depending upon the type of alcohol produced and is a nonlimiting aspect of this invention.

In a preferred embodiment, butylene is converted to butyl hydrogen sulfate and dibutyl sulfate in fat acid in this step. A number of byproducts are also produced including secondary butyl ether, carbonaceous, and polymeric particulate matter. Further acid is supplied as fat acid drawn from a subsequent reaction between butylene feed and $H_2SO_4$ such as in 8. In a most preferred embodiment, a phase separation occurs within the reactor 2, based upon the density of the products formed within it. The denser fat acid is "held back" while the less dense hydrocarbon phase proceeds to the next step of the process. This occurs until up to 90% of the reactor volume is an acid phase. This drives the reaction towards the creation of butyl hydrogen sulfate and dibutyl sulfate as butylene feed and a recycle stream of fat acid from a subsequent step are added.

In 3, the products of the reaction in 2 are phase separated into two desirable phases. One phase contains dibutyl sulfate and butyl hydrogen sulfate in fat acid. The other phase comprises hydrocarbons to include unreacted butylene and butane. The phase containing the fat acid is referred to herein as the polar phase with the phase containing butylene referred to herein as the nonpolar phase. In one embodiment, the phase separators operate at about 150 psig and 107° F. to retain butylene in the liquid state. However, any convenient combination of pressure and temperature may be selected which will retain the most volatile hydrocarbons as a liquid. Such conditions are readily selected by one skilled in the art.

Fat acid with entrained butyl hydrogen sulfate and dibutyl sulfate is removed at 4 to undergo hydrolysis at hydrolyzer 10 by the addition of water. In the embodiment described above in which butylene is reacted to form sec-butyl alcohol, over 2,000 lbs/hour of water are employed in the hydrolyzer. In a preferred embodiment of this invention the water from the hydrolysis step is used in the extraction of carbonaceous material from the rag layer. That is, a recirculation of the water allows it to be used twice; once for impurity removal and once for hydrolysis. The abundance of available water as outlined above makes this embodiment economically attractive as it increases the overall efficiency of operations.

After hydrolysis, subsequent measures are employed to finish the lower alcohol and recycle $H_2SO_4$ to the greatest extent possible. Prior art methods of indirectly hydrating olefins typically require up to 10% of the total quantity of $H_2SO_4$ to be purged from the system. The method of the instant invention allows recycling of at least 98% of the total quantity of acid. It is possible that 100% of the total quantity of acid can be recycled.

Stripping step 11 strips entrained alcohols from fat acids. In a preferred embodiment, more than one stripper is employed in series. Care must be exercised in stripping so that alcohol products do not revert to olefin in the presence of hot $H_2SO_4$. This is done by retaining the stripper conditions at appropriate pressures and temperatures as one skilled in the art would readily appreciate. For example, in one embodiment, strippers expose fat acid preheated to 150° F. to open steam. At any rate, stripping is not a critical step in the claimed process.

Acidic moieties yet remaining entrained to the lower alcohol are neutralized in step 13 and crude alcohol product is separated from other products in step 14. In the case of the production of secondary butyl alcohol, step 14 is a debutenizer. If needed, step 12 reconcentrates $H_2SO_4$ recycled from the process. Following step 12, an $H_2SO_4$ slip stream is purged to keep contaminates from building up in the process. This slip stream can be as much as 10% or more of the total recycled $H_2SO_4$. In prior art methods, 98% strength, fresh sulfuric acid was added here to make up for the purged acid. As noted above, the method of the instant invention greatly reduces the need for an acid purge and in a most preferred embodiment eliminates this step entirely.

In the embodiment of the process to make butyl alcohols, further reaction of the hydrocarbon phase separated at 3 is conducted in an additional reactor shown as 6 in FIG. 1. Essentially, this duplicates the process that occurred at reactor 2 to produce more butyl hydrogen sulfate and dibutyl sulfate which then flow through another phase separator 7. Again, two phases are formed, a polar and a nonpolar phase. Fat acid is withdrawn by extracting the polar phase which is then sent to reactor 2 before proceeding to hydrolysis at 10. It is then sent to be stripped at 11, neutralized at 13, and debutenized at 14. Crude butyl alcohol is then obtained at 15. The nonpolar phase from the separator 7 is processed back to butane or other useable reactant 9. It should also be noted that the crude butyl alcohol produced at 15 can later be finished through distillation and other treatments or it can be sent on to other processes as a reactant. For example, it is common to send the alcohol to ketone production processes such as the production of methyl ethyl ketone.

Reactors placed in stages as in FIG. 1 work to maximize the yield of the butyl alcohol that can be obtained from a given feed. Each subsequent reactor further reacts the hydrocarbon left unreacted and separated from the last $H_2SO_4$ treatment and extracted by phase separation. There is no limit to the number of stages that can be so serialized but a most preferred embodiment employs two such phases. That is, a most preferred embodiment of this method incorporates a two stage countercurrent reactor system used in the production of secondary butyl alcohol.

In the process of FIG. 1 carbonaceous and polymeric products are first produced in the reactor 2 (they are also produced in reactor 6 and other parts of the process). When the products of the reactors are phase separated at 3 and 7, polymeric and other carbonaceous species have a tendency to form as a rag layer between the polar and nonpolar polar phases therein. These substances frequently take on the form of irregularly shaped particles and readily aggregate. They may also take on the form of a powdery solid. These particles have been found to range from about 1 to greater than about 100 microns. The number average diameter is generally about 16 microns and the volume average diameter is about 135 microns. As used throughout this specification, the number average diameter is defined as the arithmetic average of all the particle diameters. We define the volume average diameter to equal the cube root of the arithmetic average of all particle volumes.

Figure 2:
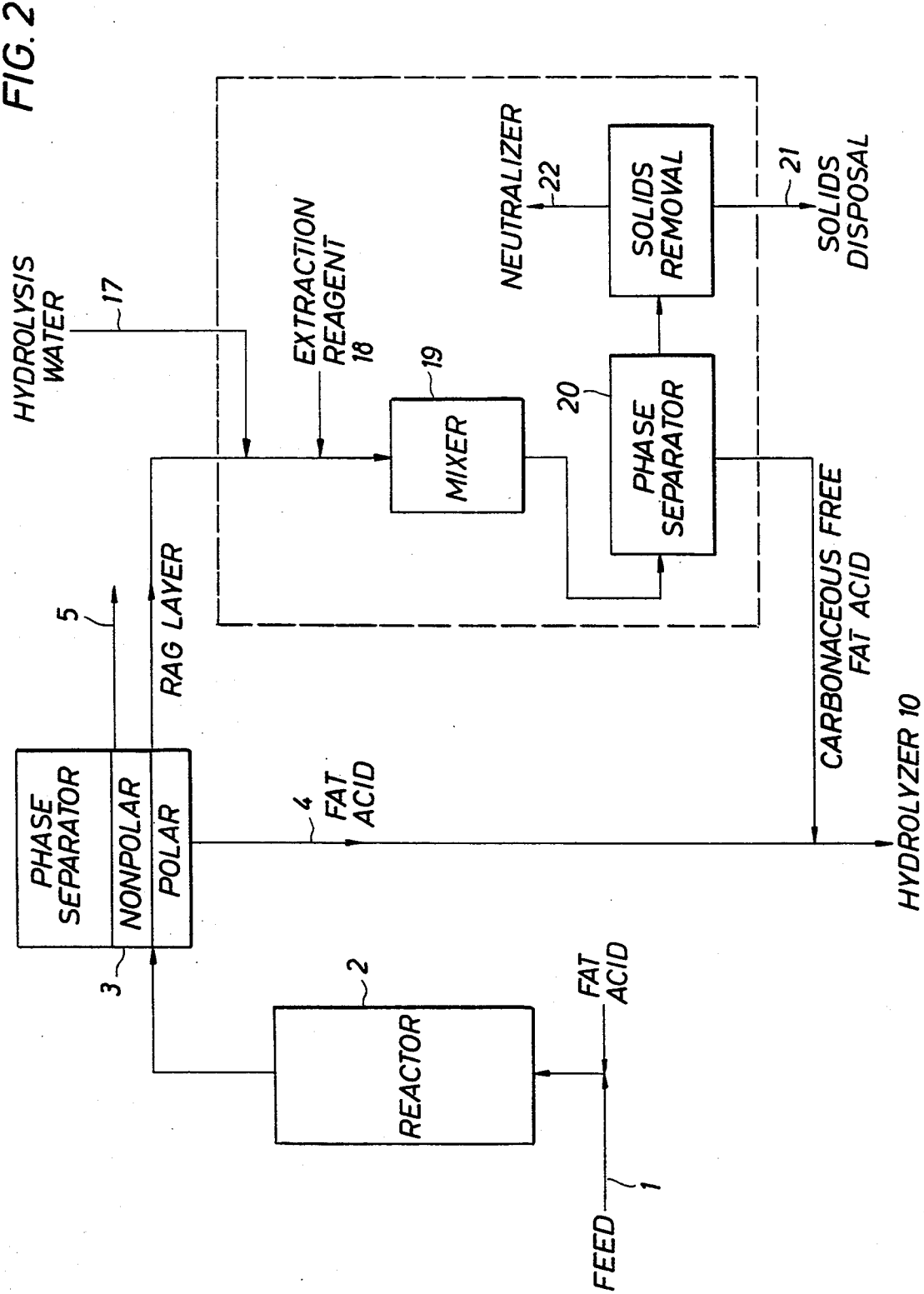
FIG. 2 is a flow diagram of a butyl alcohol production process wherein a slip stream from a subsequent step in butyl alcohol production is incorporated to extract carbonaceous impurities.

FIG. 2 shows the production of secondary butyl alcohol from butylene with the addition of the method of removing carbonaceous and polymeric byproducts of the instant invention. After the reaction of olefinic feed with sulfuric acid, the resulting products are phase separated in 3. As in FIG. 1, a nonpolar phase containing unreacted hydrocarbon lies atop a polar phase comprising butyl hydrogen sulfate and dibutyl sulfate in fat acid. A rag layer comprising carbonaceous particulate matter forms between the polar and nonpolar layers.

A slip stream 18 from a downstream product of this process is added to the rag layer. This slip stream will generally contain oligomeric or polymeric products itself. In the embodiment in which secondary butyl alcohol is produced as described above, the contents of this tops products are: 2.3% w butylene, 1.1% w water, 0.004% w methyl ethyl ketone, 0.14% w sec-butyl alcohol, 42.18% w secondary butyl ether, 38.5% w light polymers, and 15.67% w heavy polymers. Weight percents are based on the total weight of the sample of tops product. Thus, in a most preferred embodiment of this invention, the downstream product used as an extraction reaction is comprised largely of a mixture of butyl ether and $C_4$ oligomers.

Alternatively, an organic extraction reagent comprised of a solvent or a mixture of solvents can be used here. As set forth above, these may include but are not limited to toluene, 0-xylene, 1-methylnaphthalene. Other solvents which are less dense than sulfuric acid and are capable of preferentially wetting the carbonaceous particles would also be good extractants.

In a most preferred embodiment, water is also added to the slip stream from the downstream process or to the rag layer. This may be the water taken from the hydrolysis step as is the case in the most preferred embodiment of the invention or it may be added separately. The order of addition is not critical. That is, either the extractant or the water may be added first or they may be added simultaneously.

The rag layer and slip stream mixture are then mixed in a static mixer 19 or other mixing device and are then subjected to a phase separator 20. In the phase separator 20, carbonaceous-free fat acid is separated from the polymeric/particulate residue and returned to fat acid elsewhere at 4 for hydrolysis at 10. Solids are thereafter removed at 21. In the most preferred embodiment of the invention, solids form as a tops product in phase separator 20. Removal of solids from the hydrocarbon phase in step 21 can occur by sedimentation, filtration, or other process known in the art.

The invention is further described with reference to the following examples, which are intended to illustrate certain preferred embodiments without limiting its broader scope.

EXAMPLE 1

Two one quart fat acid samples were withdrawn from a first phase separator in the Shell Oil Company Norco Refinery in New Orleans, La. Aliquots of these samples were then prepared.

Butylene is hydrated to sec-butanol in the process from which the samples were taken. Two butylene/$H_2SO_4$ reactors are used; each is followed by a phase separator as discussed above. These samples were taken from the rag layer that forms between polar and nonpolar layers. Samples were depressurized to 10 psig in a sample pot and then collected in glass bottles at 0 psig. Most of the carbonaceous particles settled to the bottom of the acid but some floated near the top of the sample.

The carbonaceous particles were examined by placing drops of acid under a microscope. The particles were irregularly shaped and appeared to be aggregates of smaller particles. Most particles appeared to range in size from 1 to greater than 100 microns with the number average diameter equal to 16 microns and the volume average diameter equal to 135 microns. A second liquid phase appeared to be attached to these particles as well. The particles displayed only partial wettability with respect to the fat acid.

This example points out the existence of solid interfering substances in alcohol production processes. Further, this example shows that this carbonaceous material present in either liquid phase can have deleterious effects by leading to the entrainment of drops of one liquid into the other.

EXAMPLE 2

Fat acid samples were taken as described above. Samples were independently mixed with equal volumes of hexene, 1,7-octadiene, toluene o-xylene and 1-methylnaphthalene.

Extraction was conducted via a shake test in which samples were placed on an Eberbach platform shaker at 240 cycles per minute for 10 minutes. Relative to the fat acid, carbonaceous particles favored partitioning into the aromatic liquids but not into the olefins. When aromatics were used, greater than ninety percent of the particles were extracted from the fat acid. The relative ability of each hydrocarbon solvent to extract carbonaceous material from fat acid was as follows:

hexene < 1,7-octadiene < < o-xylene < 1-methylnaphthalene < toluene.

Mixtures containing 5 and 50 volume percent toluene gave similar results. However, with only 5 volume percent toluene, a small amount of the carbonaceous particles was left either dispersed in or settled to the bottom of the fat acid phase. This was believed to have occurred because of a lack of sufficient liquid volume to hold all of the solids. Thus, the lessened extraction at 5 volume percent is believed to be a physical phenomenon rather than a chemical phenomenon.

This example illustrates that carbonaceous material can be solvent extracted from a rag layer in a phase separator. Further, it shows that toluene is a preferred solvent in such a process.

EXAMPLE 3

Samples containing fat acid and carbonaceous particles were taken as outlined in Example 1. Aliquots were taken from one of the samples and diluted with an equal amount of water on a volume basis. Carbonaceous particles partitioned into an upper layer of the sample. These particles occupied about nine percent of the total solution volume.

Water was then added to the tops product of a downstream process from sec-butanol production (a polymer extraction step). This product contained a mixture of approximately 42% w sec-butyl ether, 54% w $C_4$ oligomers and other polymers, 2.5 w % butylene, 1% w water, and 0.5% w other miscellaneous hydrocarbons based on the total weight of tops product used. This water and tops product mixture was then added to the fat acid samples containing carbonaceous particles. The mixture of the three components was, by volume, 45% fat acid, 45% water and 10% tops product.

Each mixture separated into distinct upper and lower layers within two minutes. All of the carbonaceous material partitioned into the upper layer consisting of added hydrocarbon and material which phased out of the fat acid due to the addition of water. The additional hydrocarbons were drawn from the tops product and are largely comprised of $C_4$ compounds and their oligomers. This upper layer occupied 29 percent of the total solution volume.

This example demonstrates the increased efficacy of a water/tops product slip stream in extracting carbonaceous materials. While the tops product was itself effective, the addition of water accentuated its ability to phase out the carbonaceous materials.

EXAMPLE 4

The same procedure as outlined in example 3 was undertaken with toluene being added to fat acid samples in the place of water. A sharp toluene/acid interface formed within a minute. The upper phase was comprised of toluene and had a cloudy, tan appearance. A small amount of carbonaceous material was extracted by the toluene.

EXAMPLE 5 (HYPOTHETICAL EMBODIMENT)

Approximately 600 lbs/hour of a feed comprised of approximately 75% w n-butylene is introduced into a reactor. Approximately 550 lbs/hour of 72% w $H_2SO_4$ is added to the reactor. An average reaction temperature of 110° F. is maintained in the reactor. The contents of the reactor are subjected to a phase settler in which two phases are formed: a polar phase and a nonpolar phase. A rag layer comprising polymeric and other carbonaceous byproducts forms between the layers.

The rag layer is removed from the phase separator. An extraction reagent formed from a tops product from a subsequent polymer removal step is combined with the rag layer along with water taken from a subsequent hydrolysis step. This occurs in a static mixer. The extraction reagent is comprised of about 40% w sec-butyl ether, 55% w of oligomer and polymer derivatives of the feed, and other impurities. Weight percents are based on total weight of reagent.

Each of the components is added to the mixer so that it comprises 45% v of rag layer contents, 45% v water added from hydrolysis, and 10% v extraction reagent. Volume percents are based on total volume of the contents of the mixer. Substantially all of the polymeric and carbonaceous byproducts are then extracted in a phase separator and removed from the process. The purified acid is then returned to process for further use in the reaction.

The reacted product of $C_4$ feed and $H_2SO_4$ is then subjected to hydrolysis, stripping, and finishing. Approximately 541 lbs/hour of sec-butyl alcohol are produced substantially free of polymeric and carbonaceous impurities. $H_2SO_4$ is recirculated for use in the process without substantial diminution.

EXAMPLE 6 (HYPOTHETICAL EMBODIMENT)

The process described in example 5 is conducted with propylene in place of butylene as a feed. 70% w $H_2SO_4$ is used in place of 72% w acid. The extraction reagent is comprised of etheric, oligomeric, and polymeric derivatives of propylene. Isopropyl alcohol is produced in the process.

While this invention has been described in detail for the purpose of illustration, it is not to be construed as limited thereby but is intended to cover all changes and modifications within the spirit and scope thereof.

We claim as our invention.

1. A process for producing lower alcohols comprising:
    reacting an olefinic feed with $H_2SO_4$ in a first reactor to form a first mixture comprising alkyl sulfates, dialkyl sulfates, fat acid, and nonpolar hydrocarbons;
    separating said first mixture into two phases, a nonpolar phase comprising nonpolar hydrocarbons and a polar phase comprising alkyl sulfates, dialkyl sulfates and fat acids, said nonpolar and polar phases having therebetween a rag-layer comprising carbonaceous material;
    contacting said rag-layer with an extraction reagent so that said carbonaceous material may be removed from said process, said extraction reagent comprising ether derivative of said olefinic feed and oligomeric derivative of said olefinic feed;
    hydrolyzing said alkyl sulfates and said dialkyl sulfates to form said lower alcohol; and
    recirculating said $H_2SO_4$ to said reaction without substantial diminution.

2. A process according to claim 1 wherein said olefinic feed is comprised of butylene, said alkyl sulfate is comprised of butyl hydrogen sulfate, said dialkyl sulfate is comprised of dibutyl sulfate, said ether derivative is comprised of sec-butyl ether, said oligomeric derivative is comprised of $C_4$ oligomer, and said lower alcohol is comprised of secondary butyl alcohol.

3. A process according to claim 2 wherein said carbonaceous material is a mixture comprised of oligomeric derivatives of said olefinic feed, etheric derivatives of said olefinic feed, and sulfonates.

4. A process according to claim 2 wherein said olefinic feed is contacted with $H_2SO_4$ comprising at least 72% w by total weight of acid.

5. A process according to claim 1 wherein between about 1 and 200% v of extraction reagent is mixed with said rag layer based on the volume of the rag layer before said extraction reagent is added.

6. A process according to claim 5 wherein between about 5 and 100% v of extraction reagent is mixed with said rag layer based on the volume of the rag layer before said extraction reagent is added.

7. A process according to claim 1 wherein said ether derivative and said oligomeric derivative comprise a slip stream drawn from a step in said process for the production of lower alcohols subsequent to the reaction of olefinic feed and $H_2SO_4$.

8. A process according to claim 1 further comprising the steps of further reacting olefinic feed left unreacted in said first reactor and olefinic feed derivatives left in said hydrocarbon phase of said first phase separation with $H_2SO_4$ in a second reactor to form a second mixture comprising alkyl sulfates, dialkyl sulfates, fat acid, and nonpolar hydrocarbons; separating said second mixture into two phases, a nonpolar phase comprising nonpolar hydrocarbons and a polar phase comprising alkyl sulfates, dialkyl sulfates and fat acids; and recycling said polar phase into said first reactor.

9. A process according to claim 8 wherein a second rag layer comprising carbonaceous material forms between said polar and nonpolar phases of said second mixture further comprising the steps of:
    contacting said second rag-layer with a slip stream comprising ether derivative of said olefinic feed and oligomeric derivative of said olefinic feed from a subsequent step in said process for producing lower alcohol, together with water to thereby form a separate hydrocarbon phase;
    and extracting said carbonaceous material from said second rag layer.

10. A process for producing secondary butyl alcohol comprising:
    introducing an olefinic $C_4$ feed and $H_2SO_4$ into a reactor;
    reacting said feed and said $H_2SO_4$ in said reactor to form a mixture comprising butyl sulfates, dibutyl sulfates, and fat acid;
    separating said mixture into two phases, a nonpolar phase and a polar phase, said phases having therebetween a rag-layer comprising carbonaceous material;
    extracting said carbonaceous material by contacting said rag layer with an aromatic liquid;
    removing said carbonaceous material from said process; and
    forming secondary butyl alcohol through the hydrolysis of said butyl sulfates and said dibutyl sulfates; said reaction occurring without substantial diminution of $H_2SO_4$.

11. A process according to claim 10 wherein said aromatic liquid is comprised of toluene.

12. A process according to claim 10 wherein said $H_2SO_4$ comprises a 72% w solution by total weight of acid.

13. In a process for producing secondary butyl alcohol wherein an olefinic $C_4$ feed and $H_2SO_4$ are reacted to form butyl sulfates and 10 fat acid, said butyl sulfates and fat acid are phase separated from other hydrocarbons wherein a rag-layer comprising particulate carbonaceous matter is formed therebetween, and said butyl sulfates are then subjected to hydrolysis to form secondary butyl alcohol; a method for reducing the formation of tight emulsions between said fat acid and said hydrocarbon phase and the entrainment of unreacted hydrocarbons with fat acid comprising:

contacting said rag layer with between 1 and 100 v % of water and a slip-stream of between 1 and 200 v % from a subsequent step in said process, said slip stream comprising sec-butyl ether and $C_4$ oligomers, and substantially removing said carbonaceous matter from said process wherein v % are based on the volume of rag layer before the addition of said water or said slip-stream.

14. The process of claim 13 wherein said water is a slip stream from said hydrolysis step.

15. The process of claim 13 wherein said $H_2SO_4$ is substantially unspent.

* * * * *